United States Patent [19]

Tidey et al.

[11] Patent Number: 6,046,013
[45] Date of Patent: Apr. 4, 2000

[54] PROCESS FOR IDENTIFYING SPECIFIC ANTIBODIES ASSOCIATED WITH HLA

[75] Inventors: Leigh Ann Tidey; Michael Manouchehr Moghaddam, both of Waukesha, Wis.

[73] Assignee: GTI, Brookfield, Wis.

[21] Appl. No.: 09/122,163

[22] Filed: Jul. 24, 1998

Related U.S. Application Data

[60] Provisional application No. 60/054,470, Aug. 1, 1997.

[51] Int. Cl.⁷ ................................................. G01N 33/543

[52] U.S. Cl. ................... 435/7.21; 435/7.24; 435/7.95; 435/962; 435/967; 436/518; 436/809

[58] Field of Search ................................. 735/7.21, 7.24, 735/7.95, 962, 967; 436/518, 809

[56] References Cited

U.S. PATENT DOCUMENTS

| | | | |
|---|---|---|---|
| 5,110,726 | 5/1992 | Ogden | 435/7.21 |
| 5,180,661 | 1/1993 | Brubaker | 435/7.21 |
| 5,223,397 | 6/1993 | Pouletty | 435/7.24 |
| 5,292,641 | 3/1994 | Pouletty | 435/7.24 |
| 5,482,841 | 1/1996 | Buelow | 435/7.24 |
| 5,514,557 | 5/1996 | Moghaddam | 435/7.24 |
| 5,637,472 | 6/1997 | Granados et al. | 435/7.25 |

*Primary Examiner*—David Saunders
*Attorney, Agent, or Firm*—Mark K. Johnson

[57] ABSTRACT

A process is provided for the detection and identification of human antibody types which are specific for antigens such as platelet glycoproteins and Human Leukocyte Antigen (HLA). The process aids in detecting and identifying antibody types from a patient sample which are specific for a plurality of known glycoprotein types attached to a solid support, each glycoprotein type unique from each other and separated from each other.

11 Claims, No Drawings

องค์6,046,013

PROCESS FOR IDENTIFYING SPECIFIC ANTIBODIES ASSOCIATED WITH HLA

CROSS-REFERENCE TO RELATED APPLICATIONS

This application claims the benfit of U.S. Provisional Application Ser. No. 60/054,470, filed Aug. 1, 1997.

FEDERALLY SPONSORED RESEARCH

N/A

FIELD OF THE INVENTION

A process for the detection of antibody reactivity in biological solutions is disclosed. More particularly, a process is provided for the detection and identification of human antibody types which are specific for platelet glycoproteins such as Human Leukocyte Antigen (HLA).

BACKGROUND

In many transplantation-type situations, there is concern for differences between the allotype, especially the HLA tissue type, of a cell source and the cell recipient. Antibodies against HLA can be induced by multiple blood transfusions, pregnancy, or during a prior transplant rejection. Although these antibodies may be low titer, and difficult to detect, their presence in the blood of a potential recipient is indicative that a new transplant with matching HLA could be rejected. The determination of the presence and specificity of antibodies against foreign HLA is therefore clinically important for monitoring transplant candidates and patients. Detection assays have tested for reactivity against a panel of lymphocytes, as an initial broad screen (panel reactive antibodies, PRA testing), or may be specific for a single donor (donor specific crossmatch).

The detection of antibodies specific for HLA is useful in situations such as transplantation, and platelet transfusion. Patients awaiting transplantation of kidney, liver or other organs usually have their blood tested monthly, or at least quarterly for antibodies against HLA. Because the patients occasionally need transfusions of blood or blood products, have had a pregnancy, or have received a prior organ transplant, there is opportunity for a patient to be immunized to the HLA of other people.

In a known method, a sample is collected from a patient and tested against individual white cell samples of 40–80 different people to determine 1) if antibody has been made against foreign HLA, and 2) which antigens are detected by the patient's antibody. There are hundreds of possibilities since each person's white cells carry 8 HLA Class I tissue antigens and 2 Class II tissue antigens.

A standard technique for HLA typing and detection of anti-HLA antibodies is microlymphotoxicity, where serum containing antibodies is incubated with HLA antigen-expressing lymphocytes, then with complement. If antibodies recognize a specific HLA and attach to lymphocyte cells, the cells activate the circulatory complement components. Once activated, complement components are lytic and cause the cells to become porous and die. In some cases anti-human immunoglobulin is added to augment cell killing. When the porous cells die, they can no longer keep a dye from entering them. The technologist who looks at the cells in a microscope sees dark, swollen, dye laden cells if they are dead or bright refractile cells if they are living. The level of cytotoxicity is estimated by discriminating between dead and viable cells using various dyes. The technologist records a grade of 1, 2, 4, 6, or 8 to indicate how many of the cells in that test are dead. A grade of 8 is positive and means that 80–100% of the cells have been killed. Each grade below 8 is assigned based on the percent of dead cells observed. The number assignment is an estimate rather than an exact count.

When the cells of 40–80 different donors have been examined and the results recorded, the technologist attempts to determine what antigen(s) the dead cells have in common. The tissue types of the dead cells are compared. This method has numerous disadvantages: it is labor intensive, time consuming, requires isolation of cells, requires viable cells, is nonspecific for HLA, and requires a subjective evaluation.

Flow cytometry may also be used to detect antibody-HLA activity but has many of the same disadvantages as cytotoxicity and requires expensive instrumentation. The analysis is extremely complicated and requires several years of experience to be able to interpret successfully. One difficulty in interpretation occurs when patients have multiple HLA antibodies at one time. In those instances, all cells in the test receive a grade of 8 which means that no antibodies can be identified since all tests are equally positive. In these cases, the antibody is called "multispecific".

Therefore it is important to provide alternative techniques which can be performed simply, can be automated, do not share the shortcomings described, provide a readily discernible result which is significant for the prognosis of transplant acceptance, and are comparable to data from existing tests.

Methods of HLA typing have been previously described. U.S. Pat. No. 5,223,397 describes a method of determining HLA cross match with a soluble form of HLA molecules found in biological samples. U.S. Pat. No. 5,292,641 describes the detection on a solid support of HLA or HLA specific antibodies using antigen shed from cell surfaces, called soluble antigen.

SUMMARY

Described, in one preferred embodiment, is a process for detecting and identifying human antibody types which are specific for platelet glycoproteins, comprising, attaching a plurality of glycoprotein types to a solid support, each type unique from each other and separated from each other. Then testing each glycoprotein type for background specific to that glycoprotein and measuring a numerical value for each glycoprotein type; attaching a pool of the different glycoprotein types to the solid support; testing the glycoprotein pool for background and measuring a negative control numerical value for the glycoprotein pool. Finally, calculating a background adjustment factor for each glycoprotein type wherein each glycoprotein type numerical value is mathematically related to the glycoprotein negative control numerical value.

The process further comprises testing a patient sample against each of the different glycoprotein types to obtain a numerical value for each glycoprotein type. Then determining a second negative control numerical value; obtaining a cutoff value for each respective glycoprotein type by calculating the negative control value using each respective background adjustment factor. Finally, comparing each glycoprotein type numerical value with its respective cutoff value such that when the glycoprotein type numerical value is greater than the cutoff value, antibody specific to the respective glycoprotein is suspected.

The process further comprising subtracting the cutoff value for each glycoprotein type from the respective patient sample numerical value to obtain an antibody comparison measurement associated with each glycoprotein. Then ordering the antibody comparison measurements from largest to smallest. Finally, comparing the glycoprotein types associated with each antibody comparison measurement to adjacent glycoprotein types.

In another preferred embodiment, a process is described for detecting antibody types from a patient sample which are specific for a plurality of known glycoprotein types attached to a solid support, each glycoprotein type unique from each other and separated from each other, comprising testing the patient sample against each glycoprotein type. Then obtaining a numerical patient sample value for each glycoprotein type tested, the patient sample value comprising the detected presence of antibody and background; testing a known negative sample to obtain a negative control value; calculating a cutoff value by using a mathematical relationship between the negative control value and a predetermined background adjustment factor that is specific to each glycoprotein type. Finally, comparing each patient sample value with the cutoff value for determining if antibody specific for the related glycoprotein type are present.

In yet another preferred embodiment, described is a kit for assisting detection and identification of human antibody types which are specific for glycoprotein types, comprising a solid support having a plurality of glycoprotein types attached and a background adjustment factor.

Further objects, features, and advantages of the invention will be apparent from the following detailed description when taken in conjunction with the accompanying drawings.

DETAILED DESCRIPTION

An alloantigen is a product of an allele which may be detected as an antigen by another member of the same species. The products of such alleles include polypeptides, but also specific polysaccharides and lipids synthesized by allele encoded enzymes. Of special interest are platelet glycoproteins and histocompatibility antigens which include major histocompatibility antigen groups, known as HLA in humans.

HLA is present on all nucleated cells. It is also found on platelets which are derived from nucleated cells. HLA is sometimes shed from cell surfaces and circulates in plasma. This type of HLA is sometimes called soluble antigen and is considered differently from cell membrane antigen.

Reactivity between HLA and HLA-specific binding molecules generally results in the formation of HLA-binding molecule complexes. Further, one or more binding molecules may associate with one or more BLA, though, generally, HLA- binding molecule complexes include at least one molecule of HLA or fragment thereof combined with at least one binding molecule. Various classes of binding molecules may be considered with the invention. Preferred binding molecules are HLA-specific binding molecules. HLA-specific binding molecules are molecules which are capable of reacting with, or preferentially associating with specific epitopes found in HLA. Preferably, these binding molecules associate with antigen by non-covalent binding.

The term samples, as used herein, include biological solutions such as blood, saliva, lymph and the like; organ or tissue culture derived solutions; and solutions extracted from physiological tissues. Also included in the term are derivatives and fractions of such fluids. Preferred samples are physiological solutions such as blood or derivatives thereof, serum or plasma, with or without dilution.

As used herein, a transplant recipient is an individual to whom tissue or cells from another individual (donor), generally of the same species, has been transferred. Donor tissue may also be extracted from deceased individuals where the tissue is viable at the time of transplanting.

By transplanting it is meant that the donor tissue is joined with the transplant recipient's body. Preferred transplants include the transplantation of cells, tissues and organs. Of special interest are the transfusion of blood or blood components, the transplanting of bone, skin, bone marrow, etc., and the transplantation of tissues of the pancreas, liver, kidney, heart, brain, bowel, lung, etc.

Insoluble supports may be any compositions to which HLA and antigen-binding molecules can be bound, which is readily separated from other material, and which is otherwise compatible with the overall method of measuring binding. The surface of such supports may be solid or porous and of any convenient shape. Examples of suitable insoluble supports to which the receptor is bound include beads, membranes and microtiter plates. These are typically made of glass, plastic (e.g. polystyrene), polysaccharides, nylon or nitrocellulose. Microtiter plates are especially convenient because a large number of assays can be carried out simultaneously, using small amounts of reagents and samples.

Before adding samples, any non-specific binding sites on the insoluble support i.e. those not occupied by antibody, are generally blocked. Preferred blocking agents include non-interfering proteins such as bovine serum albumin, casein, gelatin, and the like. Alternatively, several detergents at non-interfering concentrations, such as Tween, NP40, TX100, and the like may be used.

Measuring the concentration of HLA binding molecules may be accomplished by a variety of specific assays. In a preferred embodiment, an ELISA sandwich type assay is used, similar to conventional immunoassays for cross match testing. A sandwich assay is performed by first attaching a capture agent specific for the HLA to a solid support. The capture agent may be bound to the surface by any convenient means, depending upon the nature of the surface. Where the capture agent is antibody, it may be bound to the plates covalently or non-covalently.

In a preferred embodiment, a microtiter plate or strip includes a hydrazide surface that is intended to covalently interact with biomolecules such as HLA binding antibodies. This interaction immobilizes antibody on the surface in a site-directed manner which allows specific orientation of the biomolecule to enhance immunologic activity. Hydrazide coated plates may be purchased from Corning Costar Corporation (Cambridge, Mass.) including instructions for preparing and attaching binding molecules.

Useful capture agents are antibodies against the HLA. Instead of whole or intact antibodies, one may use antibody fragments, e.g., Fab, F(ab').sub.2, light or heavy chain fragments, etc. The antibodies may be specific to epitopes conserved across a class of HLA molecules or specific to an epitope expressed by a subset of HLA molecules. The antibodies may be directed to a constant region or a portion of the polymorphic region of specific alleles. In a preferred embodiment, the binding molecules are antibodies specific to HLA Class I molecules. The antibodies are attached to the hydrazide molecules coating the well surface. Such antibodies may be polyclonal or monoclonal and are generally commercially available or alternatively, readily produced by techniques known to those skilled in the art.

In a preferred embodiment, forty different HLA Class I molecules are added to wells of a solid support and captured by the binding molecules. The location of each type of HLA molecule on the plate is noted for identification purposes. Serum from a person suspected of having antibodies specific to HLA may be placed into the wells containing known HLA molecules. Then a detection process is performed to determine if antibodies specific to HLA are actually present.

However, HLA reactivity with anti-HLA antibodies from blood must be greater than background resulting from the high level of non-specific antibodies present and other interfering biochemical macromolecules found in blood. In particular, each HLA preparation has its own degree of background. Most ELISA tests are made from only one antigen. For example, in testing for hepatitis, all wells contain the same hepatitis antigen so the background remains uniform throughout. When the HLA of forty different donors is included in one assay with different background levels for each antigen, the cutoff value has to be high enough to make sure that any background will not be misinterpreted as a false positive result compromising specificity. The cutoff value is defined as the level above which indicates a positive result (significant number of patient antibodies specific to HLA) and below which indicates a negative result (not significant number of specific antibodies). Cutoff values in the preferred embodiment are determined by multiplying the negative control value obtained by two.

The present invention provides a process which accounts for the background from each of forty different HLA molecules. To obtain the HLA preparations required, forty different HLA types are chosen from many potential donors, each for possessing a specific grouping of glycoprotein that is a potential target for an antibody of an immunized person. In a preferred embodiment, a specific HLA glycoprotein from one donor is bound to a microtiter well; i.e., using forty wells of a microtiter plate, each well contains a glycoprotein preparation from one of forty donors.

To determine a value for the background of each HLA, the serum from two to fifty persons who have not been immunized is tested against wells containing HLA preparation. An immunized person is one that has had the opportunity to develop antibodies to HLA because of a prior blood transfusion or other medical procedure. Therefore, the non-immunized persons should not have developed antibodies to the HLA. After an incubation period, the wells are washed and a detection process is performed to provide a numerical value which is recorded for each serum and each well. The measurement is indicative of the background level since antibodies specific for HLA should not be present.

The presence of any antibodies binding to HLA is detected with a labeled reagent, particularly anti-human antibodies, e.g. antisera. In a preferred embodiment, anti-human antibodies are labeled with a covalently bound enzyme capable of providing a detectable signal after addition of a suitable substrate. One enzyme, Alkaline phosphatase, is preferred and reacts with PNPP (p-nitrophenyl phosphate), a substrate used with alkaline phosphatase to produce a measurable color under appropriate reaction conditions. The color intensity, using a constant reaction time, is proportional to the amount of enzyme attached to the well which is further indicative of the amount of background captured to each well. Light absorbance between about 400 to 420 nm is measured with a spectrophotometer. The color measurement that develops in each well with each normal (non-immunized) serum is recorded and an average is obtained for all 40 wells. Examples of other suitable enzymes for use in conjugates include horseradish peroxidase, alkaline phosphatase, malate dehydrogenase and the like. Examples of labels which permit direct measurement of antibodies include radiolabels, fluorephores, dyes, beads, chemilumninescers, colloidal particles, and the like. Appropriate substrates for other enzyme conjugates and suitable reaction conditions are known to those skilled in the art.

At the same time the two to fifty non-immunized sera are tested against each of the forty different HLA preparations, a negative control is tested in wells containing a pool of HLA obtained from five to one hundred random donors. Negative control serum from two or more non-immunized donors is added to at least one but preferably four negative control wells. Each well contains the pooled antigen captured by antibody which are bound to hydrazide molecules attached to the well surface. The negative control serum is incubated for a period of time sufficient to allow antibody to bind to the well. After a suitable time the wells are washed to remove non-binding molecules. After the wells are washed, anti-human antibody linked alkaline phosphatase is added to the well and incubated to allow it to attach to any bound negative control serum antibody. The wells are washed again to remove unbound antihuman antibody. Then the enzyme substrate, PNPP is added and after an appropriate time interval, the resulting color is measured. This measurement is the negative control. A new negative control is determined again in the same way with each new test.

The numerical background measurement obtained from each of the forty wells containing a specific HLA preparation tested against normal serum is divided by the average obtained for the negative control wells in that test. This calculation provides a numerical ratio indicating an expected background value to be obtained from a single HLA well compared to an average negative control value. The ratio is termed a background adjustment factor and is used to calculate a probable background for each well without having to individually test all forty wells with each assay, saving time while providing improved HLA antibody identification.

An example of a preferred embodiment, the negative control average value from four wells is the reference point. If the numerical background measurement obtained from one of the forty wells is 1.2 times higher than the negative control, 1.2 becomes a background adjustment factor. This process is repeated for all forty individual HLA preparations attached to a microtiter plate so that a background adjustment factor is obtained for each of the forty wells.

In a preferred embodiment, kits are provided which contain a previously determined background adjustment factor along with a negative control serum solution. The negative control average value is determined for each test by a kit user. However, the background adjustment factor is predetermined and included with the test kit. When the user obtains the negative control value, he is instructed to multiply it by the background adjustment factor supplied for each HLA glycoprotein to obtain a singular cutoff value for each of the forty HLA containing wells.

More particularly, a kit of the present invention provides a microtiter plate having 45 wells coated with hydrazide-antibody bound HLA. Forty wells contain individual HLA, 5 wells contain pooled HLA: 4 of which are used for the negative control and 1 for a positive control. Instructions are provided to obtain an optical density (OD) value for each of the forty wells containing individual HLA and an OD value for the 4 wells containing negative control. The OD value for the negative control is performed as previously stated using the non-immunized serum provided. A sample of a patient serum is incubated for a suitable time in each of the forty wells containing known HLA molecules previously attached to the hydrazide well. At the same time, the negative control serum is added to the designated negative control wells and a positive control serum (serum that is known to contain antibody specific for pooled HLA) is added to the designated positive control well. The wells are washed to remove non-specific antibody. Alkaline Phosphatase is then incubated in each well and washed after a suitable time. The substrate is added and any resulting OD is measured and recorded.

To determine the cutoff value distinguishing positive from negative results for each antigen, the user multiplies the conversion factor times the negative control. For example:

| Well containing | Background Adjustment Factor | Mean of Negative Control × 2 | Cutoff Value | OD for Patient Sample | Interpretation |
|---|---|---|---|---|---|
| HLA prep 1 | 1.2 × .090 = .108 | | | .150 | Positive |
| HLA prep 2 | 1.4 × .090 = .126 | | | .100 | Negative |

By using a conversion factor, the naturally occurring background is mathematically removed. This accounts for the background contributed by each antigen and replaces the need for testing a negative control against each antigen every time the test is performed. This process has proven successful in tests identifying patient antibody.

Once an OD result is obtained for each well, the specific type of antibody attached to an HLA must be identified. The user compares the known HLA antigens that are present in the positive wells to determine which tissue HLA antigens they have in common.

The following examples are given to further illustrate the preferred embodiments of the invention.

EXAMPLES

EXAMPLE 1

A full microplate is required comprised of 12 1×8 microwell strips—enough for 2 samples. The strips are color coded according to their final location in the frame when the test is run. Each color coded strip has different lysates in each well.

EXAMPLE 2

Monoclonal antibody, prepared by standard techniques, will be added to each well in the following configuration:

|   | yellow 1 | green 2 | blue 3 | purple 4 | red 5 | orange 6 | 7 | 8 | 9 | 10 | 11 | 12 |
|---|---|---|---|---|---|---|---|---|---|---|---|---|
| A | | | | | | | | | | | | |
| B | | | | | | | | | | | | |
| C | | | | | | | | | | | | |
| E | | | | | | | | | | | | |
| F | | | | | | | | | | | | |
| G | | | | | | | | | | | | |
| H | | | | | | | | | | | | |

Add 50 μL to each well according to the layout above with one exception. Do not add monoclonal antibody to the F, G and H rows of the strips to be colored orange. When all of the antibody has been added, seal the plates with tape to prevent evaporation. Incubate the plates overnight at 2–8° C.

Wash the plates two times with wash solution and add 200 μL of blocking buffer to each well in the same configuration as antigen and monoclonal antibody application. Incubate the plate at 20–25° C. (room temp.) for one hour. Wash the frames once more using wash solution.

Add 50 μL of diluted HLA preparation obtained by solubilizing the HLA antigen from human platelets to the appropriate wells according to the following:

| Yellow Strips: | Green Strips: |
|---|---|
| Row A Donor 1 | Row A Donor 9 |
| Row B Donor 2 | Row B Donor 10 |
| Row C Donor 3 | Row C Donor 11 |
| Row D Donor 4 | Row D Donor 12 |
| Row E Donor 5 | Row E Donor 13 |
| Row F Donor 6 | Row F Donor 14 |
| Row G Donor 7 | Row G Donor 15 |
| Row H Donor 8 | Row H Donor 16 |
| Blue Strips: | Purple Strips: |
| Row A Donor 17 | Row A Donor 25 |
| Row B Donor 18 | Row B Donor 26 |
| Row C Donor 19 | Row C Donor 27 |
| Row D Donor 20 | Row D Donor 28 |
| Row E Donor 21 | Row E Donor 29 |
| Row F Donor 22 | Row F Donor 30 |
| Row G Donor 23 | Row G Donor 31 |
| Row H Donor 24 | Row H Donor 32 |
| Red Strips: | Orange Strips: |
| Row A Donor 33 | Row A Donor Pooled |
| Row B Donor 34 | Row B Donor Pooled |
| Row C Donor 35 | Row C Donor Pooled |
| Row D Donor 36 | Row D Donor Pooled |
| Row E Donor 37 | Row E Donor Pooled |
| Row F Donor 38 | Row F Donor none |
| Row G Donor 39 | Row G Donor none |
| Row H Donor 40 | Row H Donor none |

Incubate at 20–25° C. for 1 hour.

Wash each plate 3 times and add 100 μL of a commercial stabilizing agent to all of the wells except Orange rows G and H and allow the plates to stand at room temperature for 50–60 minutes. Decant the solution and invert the plates on a towel for a few moments then let dry for about 60 minutes. To complete the drying process, place the plates of strips in a vacuum desiccator containing desiccant for at least 48 hours.

EXAMPLE 3

Using a preferred embodiment of a kit, approximately 100 mL of wash solution will be required for each sample to be tested. Remove the microtiter frame and strips from the protective foil pouch. If only one sample is to be tested, remove one strip of each color from the frame and reseal the remaining strips in the pouch. Add 250 μL of wash solution to all wells and allow to stand at room temperature for 5–10 minutes.

Decant or aspirate the contents of each well. Invert plate and blot on absorbent material to remove any residual fluid. For each sample to be tested, dilute the negative and positive control, and the patient sample as follows: add 60 μL of Negative Serum Control to 180 μL of Specimen Diluent Solution; add 30 μL of Positive Serum Control to 90 μL of Specimen Diluent Solution; add 550 μL of each patient serum or plasma sample to 1650 μL of Specimen Diluent Solution provided. Mix each dilution thoroughly.

Add 50 μL of diluted Positive Serum Control sample to well E of the orange strip. Add 50 μL of diluted Negative Serum Control sample to wells A through D of the orange strip. Add 50 μL of diluted patient sample to all of the wells in all strips except the orange strip. Add patient sample only to well F of the orange strip. Wells F, G and H of the orange strip do not contain any antigen, Wells G and H are to be used as Blank Controls. Cover the strips tightly with plate sealer and incubate at 37° C. for 30–35 minutes. If a 37° C. dry incubator is used, increase the incubation time by 10 minutes.

Decant or aspirate the contents of each well. Add 200–300 μL of wash solution, then decant or aspirate. Repeat this sequence three more times for a total of four washes. Invert the plate and blot it on an absorbent material to remove any residual fluid. For each sample to be tested, add 30 μL anti-IgG to 3.0 mL of Specimen Diluent for a 1:100 dilution. Mix well. Add 50 μL of diluted anti-IgG to all wells except the wells G and H of the control (orange) strip. Cover the plate with a plate sealer and incubate at 37° C. for 30–35 minutes. If a 37° C. dry incubator is used, increase the incubation time by 10 minutes.

Repeat the wash step above, then prepare P-nitrophenyl phosphate (PNPP) substrate by dissolving crystalline powder with 0.5 mL of deionized water. For each sample to be tested, add 50 μL of PNPP solution to 5.0 mL of Enzyme Substrate Buffer. Mix thoroughly and keep away from direct light. This reagent should be used immediately after preparation. Add 100 μL of the diluted PNPP solution to all of the wells except the wells G and H of the control (orange) strip. Allow the plate to stand in the dark for 30 minutes at 20–25° C. To stop the reaction, add 100 μL of ELISA Stopping solution (3M NaOH Solution) to all of the wells in all strips. Add an additional 100 μL of Stopping Solution to the wells G and H of the control (orange) strip. These wells will be used as blanks. Read the absorbance (OD) of each well at 405 or 410 nm within 15 minutes of stopping the reaction.

Interpretation

Calculate a preferred cutoff value for each individual well as follows:

Mean of negative control wells (A, B, C, & D of orange strip)×2×background conversion factor=Cutoff value for the well.

Test results with OD values equal to or greater than the cutoff value are regarded as positive results. Test results with OD values less than the cutoff value are considered negative.

Calculate the percent PRA (Panel Reactive Antibody) as follows:

$$\% \ PRA = \frac{\# \ of \ Positive \ Results \times 100}{40}$$

EXAMPLE 4

| DONOR | HLA TYPE | Backgrnd Conversn Factor (BCF) | Negative Serum OD | BCF x Neg. Serum OD x 2 | Patient Serum OD | Patient Serum OD minus Cutoff |
|---|---|---|---|---|---|---|
| 1 | 33, X, 14, 53(4, 6)4, z | 1.591 | 0.062 | 0.197 | 0.126 | ****** |
| 2 | 28, 33, 14, 42(—, 6)7, z | 1.736 | 0.062 | 0.215 | 0.139 | ****** |
| 3 | 41, 2, 51, 63(4, —)4, z | 1.217 | 0.062 | 0.151 | 0.072 | ****** |
| 4 | 24, 8, 50(—, 6)6, 7 | 1.232 | 0.062 | 0.153 | 0.225 | 0.072 POS |
| 5 | 74, 18, 71(—, 6)3, z | 1.718 | 0.062 | 0.213 | 0.153 | ****** |
| 6 | 28, 29, 52, 81(4, 6)6, 7 | 1.246 | 0.062 | 0.155 | 0.104 | ****** |
| 7 | 28, 30, 52, 81(4, 6)7, z | 1.870 | 0.062 | 0.232 | 0.143 | ****** |
| 8 | 29, 34, 44, 60(4, 6)4, z | 1.813 | 0.062 | 0.225 | 0.199 | ****** |
| 9 | 3, 33, 71, 78(—, 6)4, z | 1.079 | 0.062 | 0.134 | 0.836 | 0.702 POS |
| 10 | 32, 34, 44, 60(4, 6)3, 4 | 1.585 | 0.062 | 0.197 | 0.173 | ****** |
| 11 | 2, 32, 37, 49(4, —)6, 7 | 1.413 | 0.062 | 0.175 | 0.118 | ****** |
| 12 | 3, 66.1, 45, 62(—, 6)4, z | 1.499 | 0.062 | 0.186 | 0.485 | 0.299 POS |
| 13 | 3, 36, 57, 63(4, —)6, z | 1.356 | 0.062 | 0.168 | 0.525 | 0.357 POS |
| 14 | 1, 26, 55, 62(—, 6)3, 4 | 1.780 | 0.062 | 0.221 | 0.106 | ****** |
| 15 | 3, 11, 35, 56(—, 6)4, z | 1.749 | 0.062 | 0.217 | 0.639 | 0.422 POS |
| 16 | 24, 32, 51, 56(4, 6)1, z | 1.845 | 0.062 | 0.229 | 0.126 | ****** |
| 17 | 24, 26, 7, 14(—, 6)7, 8 | 1.598 | 0.062 | 0.198 | 0.134 | ****** |
| 18 | 23, 68, 49, 60(4, 6)3, z | 1.610 | 0.062 | 0.200 | 0.106 | ****** |
| 19 | 2, 66.1, 41, 45(—, 6)z, z | 1.063 | 0.062 | 0.132 | 0.128 | ****** |
| 20 | 2, 26, 61, 62(—, 6)9, z | 1.077 | 0.060 | 0.134 | 0.067 | ****** |
| 21 | 2, X, 44, 48(4, 6)5, z | 1.130 | 0.062 | 0.140 | 0.068 | ****** |
| 22 | 11, 25, 18, 60(—, 6)3, z | 1.245 | 0.062 | 0.154 | 0.189 | 0.035 POS |
| 23 | 36, 74, 58, 72(4, 6)2, z | 1.025 | 0.062 | 0.127 | 0.118 | ****** |
| 24 | 2, 25, 8, 27(4, 6)1, 7 | 1.047 | 0.062 | 0.130 | 0.238 | 0.108 POS |
| 25 | 2, 31, 27, 57(4, —)2, 7 | 1.082 | 0.062 | 0.134 | 0.115 | ****** |
| 26 | 31, 3, 35, 37(4, 6)4, 6 | 1.023 | 0.062 | 0.127 | 0.918 | 0.791 POS |
| 27 | 2, 23, 13, 35(4, 6)z, z | 1.349 | 0.062 | 0.167 | 0.085 | ****** |
| 28 | 66.2, X, 35, 70(—, 6)3, 4 | 1.043 | 0.062 | 0.129 | 0.180 | 0.051 POS |
| 29 | 1, 25, 39, 58(4, 6)7, z | 1.570 | 0.062 | 0.195 | 0.089 | ****** |
| 30 | 1, 29, 8, 44(4, 6)7, z | 1.886 | 0.062 | 0.234 | 0.349 | 0.115 POS |

-continued

| DONOR | HLA TYPE | Backgrnd Conversn Factor (BCF) | Negative Serum OD | BCF × Neg. Serum OD × 2 | Patient Serum OD | Patient Serum OD minus Cutoff |
|---|---|---|---|---|---|---|
| 31 | 1, 3, 8, 35(—, 6)4, 7 | 1.862 | 0.062 | 0.231 | 0.925 | 0.694 POS |
| 32 | 2, X, 38, 46(4, —)1, 7 | 1.655 | 0.062 | 0.205 | 0.085 | ****** |
| 33 | 3, 30, 35, 57(4, 6)4, z | 1.587 | 0.062 | 0.197 | 0.837 | 0.640 POS |
| 34 | 1, 31, 7, 67(—, 6)2, 3 | 1.498 | 0.062 | 0.186 | 0.111 | ****** |

Pos Control 1.605

In this example, there are twelve positive reactions. The reactions correspond to a set of eight different HLA antigens for each positive reaction. The user must decide which antigen the twelve sets have in common. The first three positive reactions represent the following sets:

| A Locus | | B Locus | | Bw Locus | | C Locus | |
|---|---|---|---|---|---|---|---|
| 2 | 24 | 8 | 50 | — | w6 | 6 | 7 |
| 3 | 33 | 71 | 78 | — | w6 | 4 | z |
| 3 | 66.1 | 45 | 62 | — | w6 | 4 | z |

At this point, the antibody could be against w6 since all three cells are positive for w6 If three more cells are added:

| A Locus | | B Locus | | Bw Locus | | C Locus | |
|---|---|---|---|---|---|---|---|
| 3 | 36 | 57 | 63 | w4 | — | 6 | z |
| 3 | 11 | 35 | 56 | — | w6 | 4 | z |
| 11 | 25 | 18 | 60 | — | w6 | 3 | z |

At this point, none of the antigen sets have one item in common. Therefore, this patient sample must contain a mixture of the HLA antibodies. By just assigning a positive result, there is no way to give more weight to some positives than others. When this identification is performed using cytotoxicity, the reactions are graded but the grading system is crude and often only the grade of 8 (strong positive reactions) is seen. Many patient samples are called "multi-specific" because all reactions are strong positive and no single antibody can be recognized in the mixture.

We have devised a more precise method for the analysis of results. By determining how much stronger (or weaker) a reaction is compared to the cutoff, an infinite number of grades of antibody reactions can be assigned, making it much easier to sort and identify the antibodies. By subtracting the cutoff value for each well from the patient result for that well, a difference is obtained in OD units. Then, if the results are sorted with the greatest difference at the top, antibodies against one antigen will group together. For example:

EXAMPLE 4

| DONOR | HLA TYPE | BCF | Negative Serum OD | BCF × Neg. Serum OD × 2 | Patient Serum OD | Patient Serum OD minus Cutoff | Pos or Neg |
|---|---|---|---|---|---|---|---|
| 26 | 1, 3, 35, 37(4, 6)4, 6 | 1.023 | 0.062 | 0.127 | 0.918 | 0.791 | POS |
| 9 | 3, 33, 71, 78(—, 6)4, z | 1.079 | 0.062 | 0.134 | 0.836 | 0.702 | POS |
| 31 | 1, 3, 8, 35(—, 6)4, 7 | 1.862 | 0.062 | 0.231 | 0.925 | 0.694 | POS |
| 33 | 3, 30, 35, 57(4, 6)4, z | 1.587 | 0.062 | 0.197 | 0.837 | 0.640 | POS |
| 15 | 3, 11, 35, 56(—, 6)4, z | 1.749 | 0.062 | 0.217 | 0.639 | 0.422 | POS |
| 13 | 3, 36, 57, 63(4, —)6, z | 1.356 | 0.062 | 0.168 | 0.525 | 0.357 | POS |
| 12 | 3, 66.1, 45, 62(—, 6)4, z | 1.499 | 0.062 | 0.186 | 0.485 | 0.299 | POS |
| 30 | 1, 29, 8, 44(4, 6)7, z | 1.886 | 0.062 | 0.234 | 0.349 | 0.115 | POS |
| 24 | 2, 25, 8, 27(4, 6)1, 7 | 1.047 | 0.062 | 0.130 | 0.238 | 0.108 | POS |
| 4 | 2, 24, 5, 50(—, 6)6, 7 | 1.232 | 0.062 | 0.153 | 0.225 | 0.072 | POS |
| 28 | 66.2, X, 35, 70(—, 6), 4 | 1.043 | 0.062 | 0.129 | 0.180 | 0.051 | POS |
| 22 | 11, 25, 18, 60(—, 6)3, z | 1.245 | 0.062 | 0.154 | 0.189 | 0.035 | POS |
| 19 | 2, 66.1, 41, 45(—, 6)z, z | 1.063 | 0.062 | 0.132 | 0.128 | −0.00 | NEG |
| 23 | 36, 74, 58, 72(4, 6)2, z | 1.025 | 0.062 | 0.127 | 0.118 | −0.009 | NEG |
| 25 | 2, 31, 27, 57(4, —)2, 7 | 1.082 | 0.062 | 0.134 | 0.115 | −0.019 | NEG |
| 10 | 32, 34, 44, 60(4, 6)3, 4 | 1.585 | 0.062 | 0.197 | 0.173 | −0.024 | NEG |
| 8 | 29, 34, 44, 60(4, 6)4, z | 1.813 | 0.062 | 0.225 | 0.199 | −0.026 | NEG |
| 6 | 28, 29, 52, 81(4, 6)6, 7 | 1.246 | 0.062 | 0.155 | 0.104 | −0.051 | NEG |
| 11 | 2, 32, 37, 49(4, —)6, 7 | 1.413 | 0.062 | 0.175 | 0.118 | −0.057 | NEG |
| 5 | 28, 74, 18, 71(—, 6)3, z | 1.718 | 0.062 | 0.213 | 0.153 | −0.060 | NEG |
| 17 | 24, 26, 7, 14(—, 6)7, 8 | 1.598 | 0.062 | 0.198 | 0.134 | −0.064 | NEG |
| 20 | 22, 26, 61, 62(—, 6)9, z | 1.077 | 0.062 | 0.134 | 0.067 | −0.067 | NEG |
| 1 | 33, X, 14, 53(4, 6)4, z | 1.591 | 0.062 | 0.197 | 0.126 | −0.071 | NEG |
| 21 | 2, X, 44, 48(4, 6)5, z | 1.130 | 0.062 | 0.140 | 0.068 | −0.072 | NEG |

-continued

| DONOR | HLA TYPE | BCF | Negative Serum OD | BCF × Neg. Serum OD × 2 | Patient Serum OD | Patient Serum OD minus Cutoff | Pos or Neg |
|---|---|---|---|---|---|---|---|
| 34 | 1, 31, 7, 67(—, 6)2, 3 | 1.498 | 0.062 | 0.186 | 0.111 | −0.075 | NEG |
| 2 | 28, 33, 14, 42(—, 6)7, z | 1.736 | 0.062 | 0.215 | 0.139 | −0.076 | NEG |
| 3 | 1, 2, 51, 63(4, —)4, z | 1.217 | 0.062 | 0.151 | 0.072 | −0.079 | NEG |
| 27 | 2, 23, 13, 35(4, 6)z, z | 1.349 | 0.062 | 0.167 | 0.085 | −0.082 | NEG |
| 7 | 28, 30, 52, 81(4, 6)7, z | 1.870 | 0.062 | 0.232 | 0.143 | −0.089 | NEG |
| 18 | 23, 68, 49, 60(4, 6)3, z | 1.610 | 0.062 | 0.200 | 0.106 | −0.094 | NEG |
| 16 | 24, 32, 51, 56(4, 6)1, z | 1.845 | 0.062 | 0.229 | 0.126 | −0.103 | NEG |
| 29 | 1, 25, 39, 58(4, 6)7, z | 1.570 | 0.062 | 0.195 | 0.089 | −0.106 | NEG |
| 14 | 1, 26, 55, 62(—, 6)3, 4 | 1.780 | 0.062 | 0.221 | 0.106 | −0.115 | NEG |
| 32 | 2, X, 38, 46(4, —)1, 7 | 1.655 | 0.062 | 0.205 | 0.085 | −0.120 | NEG |

Pos Control 1.605

By sorting the results based on the strength of the reactions, it is easy to see that the first seven antigen sets share the antigen designated as 3. The next three cells share the antigen designated as 8. The last two sets of antigen do not have either a 3 or 8 and would make the interpretation more difficult if they could not be separated from the rest. By giving each reaction its own weight, the last two antigen sets seem less significant and can be set aside while the antibody to 3 and 8 are very clear.

This method for providing forty individual HLA glycoproteins with forty individual background conversion factors and then sorting the results by optical density values compared to the individualized cutoff points facilitates antibody identification and introduces more objectivity into the interpretation process. Cytotoxicity methods can only separate positive reactions into two or sometimes three grades, 4, 6 and 8. In contrast, sorting by optical density separates the positive reactions into many grades for quickly obtaining more objective and accurate interpretation.

The foregoing is considered as illustrative only of the principles of the invention. Furthermore, since numerous modifications and changes will readily occur to those skilled in the art, it is not desired to limit the invention to the exact construction and operation shown and described. Accordingly, all suitable modifications and equivalents fall within the scope of the invention.

We claim:

1. A process for detecting and identifying human antibody types which are specific for platelet glycoproteins, comprising:
   a) attaching a plurality of glycoprotein types to a solid support, each type unique from each other and separated from each other;
   b) testing each glycoprotein type for background specific to that glycoprotein against serum from one or from a pool of multiple non-immunized donors and measuring a numerical value for each glycoprotein type;
   c) attaching a pool of the different glycoprotein types to the solid support;
   d) testing the glycoprotein pool for background against serum from one or from a pool of two or more non-immunized donors and measuring a negative control numerical value for the glycoprotein pool;
   e) dividing the glycoprotein type value obtained from step b) by the negative control value from step d) to create a background adjustment factor for each glycoprotein type;
   f) adding a sample possibly containing antibodies to each glycoprotein type attached to the solid support;
   g) calculating a cutoff value for each glycoprotein type equal to the negative control numerical value from step (d) multiplied by a numerical value background adjustment factor for each glyconrotein from step (e); and,
   h) measuring a numerical value for each glycoprotein type mixed with a sample, wherein a measured numerical value greater than the cutoff value for any glycoprotein type indicates that antibodies specific for that glycoprotein type are present.

2. The process of claim 1 wherein step a) further comprises attaching each individual glycoprotein type to an individual well of the solid support.

3. The process of claim 2 wherein the glycoprotein types are attached to the solid support with a hydrazide compound and HLA binding antibodies or HLA binding antibody fragments.

4. The process of claim 3 wherein the solid support comprises a microtiter plate.

5. The process of claim 4 wherein step b) further comprises measuring a numerical value using a serum obtained from a plurality of normal donors.

6. The process of claim 5 wherein step d) further comprises measuring a negative control numerical value using a serum obtained from two or more non-immunized donors.

7. The process of claim 5 wherein the numerical values comprise optical density measurements.

8. A process for detecting antibody types from a patient sample which are specific for a plurality of known glycoprotein types attached to a solid support, each glycoprotein type unique from each other and separated from each other, comprising:
   a) testing the patient sample against each glycoprotein type;
   b) obtaining a numerical patient sample value for each glycoprotein type tested, the patient sample value comprising the detected presence of antibody and background;
   c) testing a glycoprotein pool for background against serum from a pool of two or more non-immunized donors and measuring a negative control numerical value for the glycoprotein pool;
   d) calculating a cutoff value for each glycoprotein type by multiplying the negative control numerical value from step (c) by a predetermined background adjustment factor for each glycoprotein type; and,
   e) comparing the numerical patient sample value for each glycoprotein type determined in step (b) with the cutoff value for each glycoprotein type calculated in step (d), wherein a numerical patient value greater than or equal to the cutoff value for any glycoprotein type indicates that antibodies specific for that glycoprotein are present.

9. The process of claim 8 further comprising:

g) subtracting the cutoff value from the patient sample value to obtain an identification value related to each glycoprotein type; and, h) sorting glycoprotein types having identification values ordered from highest to lowest to identify specific antibody types.

10. The process of claim 9 wherein the solid support is a plate having one well containing each glycoprotein type.

11. The process of claim 10 wherein the values are optical density readings.

* * * * *